United States Patent
Yaccarino, III

[19]

[11] Patent Number: 6,025,538
[45] Date of Patent: Feb. 15, 2000

[54] COMPOUND BONE STRUCTURE FABRICATED FROM ALLOGRAFT TISSUE

[75] Inventor: Joseph A. Yaccarino, III, Somerset, N.J.

[73] Assignee: Musculoskeletal Transplant Foundation, Edison, N.J.

[21] Appl. No.: 09/196,251

[22] Filed: Nov. 20, 1998

[51] Int. Cl.[7] .................................. A61F 2/28; A61F 2/44
[52] U.S. Cl. ............................................... 623/16; 623/17
[58] Field of Search .................................... 623/16, 17

[56] References Cited

U.S. PATENT DOCUMENTS

| | | | |
|---|---|---|---|
| 4,858,603 | 8/1989 | Clemow et al. | 128/92 |
| 4,877,020 | 10/1989 | Vich | 128/92 |
| 4,932,973 | 6/1990 | Gendler | 623/16 |
| 5,112,354 | 5/1992 | Sires | 623/16 |
| 5,405,391 | 4/1995 | Hednerson et al. | 623/17 |
| 5,439,684 | 8/1995 | Prewett et al. | 424/422 |
| 5,571,190 | 11/1996 | Ulrich et al. | 623/17 |
| 5,798,096 | 8/1998 | Pavlyk. | |
| 5,865,848 | 2/1999 | Baker | 623/17 |
| 5,888,222 | 3/1999 | Coates et al. | 623/17 |
| 5,899,939 | 5/1999 | Boyce et al. | 623/16 |

OTHER PUBLICATIONS

F. Albee *Bone Graft Surgery in Disease, Injury and Deformity*, p. 22 (1940).
F. Albee, The Improved Albee Bone Mill, American Journal of Surgery, p. 657 (Mar., 1978).

*Primary Examiner*—Michael J. Milano
*Assistant Examiner*—Hieu Phan
*Attorney, Agent, or Firm*—John S. Hale

[57] ABSTRACT

A composite allograft bone device comprising a first bone member body defining with a face that includes a plurality of intersecting grooves cut into the face of the body to define a plurality of spaced projections forming a pattern and a second bone member body defining a face that includes a plurality of angularly intersecting grooves cut into the face to form a plurality of spaced projections forming a second pattern. The projections on the second face fit into grooves cut in the first face allowing the two bodies to be mated together with the spaced projections of each face fitting into the grooves of the opposing face. The mated bodies form a composite bone device which is provided with a throughgoing bore positioned at an angle to the longitudinal axis of the composite device and a dowel mounted in the throughgoing bore extending into the bone member bodies precluding the same from relative longitudinal movement.

46 Claims, 5 Drawing Sheets

COMPOUND BONE STRUCTURE FABRICATED FROM ALLOGRAFT TISSUE

BACKGROUND OF THE INVENTION

1. Field of Invention

The present invention generally relates to allograft bone devices for surgical implantation into bone tissue and particularly to a composite allograft bone device constructed from two or more separate bone pieces made from allograft, autograft and xenograft bone tissue that can be constructed to have dimensions that are larger than the dimensions of naturally occurring bone suitable for implantation in a surgical site.

2. Description of the Prior Art

Allograft bone tissue is widely used in orthopedic, neuro-, maxillofacial, podiatric and dental surgery. Allograft tissue is valuable in these fields of surgery because it is strong and it biointegrates well over time with the recipient patient's tissue. Allograft bone tissue can be shaped for specific surgical applications by the surgeon or by a bone product manufacturer in a manufacturing environment before the allograft bone tissue is transferred to the surgeon. Unfortunately because of the size limitation of the bone material only devices of a certain size could be constructed.

Surgical implants constructed entirely from allograft bone tissue are generally superior to implants constructed from synthetic or nonabsorbable polymers or metals because allograft bone tissue is bioinert and integrates well with the surrounding tissues.

Allograft bone occurs in two basic forms: 1) cancellous bone (also referred to as trabecular bone) and 2) cortical bone. Cortical bone is highly dense and has a compound structure comprised of calcium hydroxyapatite reinforced with collagen fiber. This cortical bone material is the predominant load bearing component of long bones in the human body. Many shapes and forms can be fabricated from allograft cortical bone tissue including pins, screws, plates, intervertebral discs and the like for use in human surgery. Cortical bone has one serious limitation that plastics and metal do not have. Bone parts and bone products made from allograft cortical tissue are limited in size, dimension and shape because of the anatomical limits on the thickness and length of the source bone.

As an example, the largest long bone, the femur bone, has a thick cortical wall that varies in thickness from about two millimeters to about ten millimeters. The majority of the femoral cortical bone wall typically ranges from about three millimeter to about eight millimeters in thickness. The length of the cortical tissue is also naturally limited by the size and the weight of the allograft tissue donor. Accordingly, specific implants fabricated from cortical bone have previously not been larger than these natural anatomical dimensions. The other long bones of the bones of the human body, the humorous, the tibia, the fibula, the radius, the ulna, the ribs, etc., are similarly limited in dimension. Shaped implants made from these other long bones are also necessarily limited in dimension.

The dimensional limit that has been achieved with single piece cortical bone is about 10 mm×about 13 mm cross-sections. The length of these sections can be much longer as they are taken from the long axis of the bone. The research that has been completed shows femoral sections ranging from 3 mm×4 mm to 10 mm×10 mm at the mid-shaft and tibial sections 3 mm×6 mm to 10 mm×13 mm at the proximal end.

Many medical problems and surgical procedures require implants larger than have previously been made out of allograft cortical tissue. It is desirable to have a surgical implant made entirely out of allograft cortical tissue that is larger than can be made from a single piece of naturally occurring bone. Two requirements must be met by any implant fabricated entirely from cortical bone, however, to achieve a successful surgical result. First, the components must be held together in such a way that the mechanical structure of the implant is not compromised during the surgical implantation procedure. Many surgical implants are implanted in the recipient patient with a large applied force. Many implants are actually hammered in as is the case for an intervertebral implant. Second, the compound structure of the implant must hold together during the post-operative period during which the allograft tissue is resorbed and remodeled.

The prior art contains many references directed to fasteners, spinal cages and devices which are constructed of inert metals or plastics which are used in bone repair. There are relatively few devices used in bone repair constructed of allograft bone because of the difficulty in obtaining and shaping the material and the natural limits placed on the size of the device based on the constraints of the sizes of the natural bone which can be shaped to form devices of a larger required size.

One example of an allograft device is disclosed in U.S. Pat. No. 4,877,020 which shows a dowel made of bone having a helicoidal thread.

Another device is shown in U.S. Pat. No. 4,932,973 where the use of a perforated bone matrix for use in insertion or implantation in a bone mass to promote bone growth is disclosed.

Similarly U.S. Pat. No. 5,112,354 discloses the preparation of an allograft bone segment for use in skeletal reconstruction. The bone segment is demineralized and a multiplicity of bores (described as pores) are drilled into the bone mass in a pattern to maximize the surface area of the implant. Some of the bores are drilled through the bone mass at the center of the hexagon pattern.

U.S. Pat. No. 5,439,684 is directed toward various swollen demineralized bone constructions such as sleeves, rectangular pledgets and wedges. The pledgets and wedges can be used as invertebrate support blocks. The bone can be machined into a desired shape for implantation such as sheet, disc, ring, cube, cylinder or sliced and wrapped into a tubular shape. However, all of these bone structures are limited to the size and shape of the original material.

Another patent of interest is U.S. Pat. No. 4,858,603 which shows a bone pin which is placed through an angular bore cut through two separate pieces of bone to hold the pieces together in a fixed secured relationship. The bone pin is made from a polymer which is absorbable in an animal body.

Until now, the only way that separate bone pieces could be joined together to arrive at a larger device has been to tongue and groove the respective pieces which creates shearing areas and limits the use to which such constructed device could be used. This is a significant problem where a device is placed under stress and shearing forces as for example where it is hammered into place between vertebrae or into other bone areas. The first disclosure of joining together separate pieces of allograft bone is believed to be set forth in various articles by F. Albee. This disclosure also show the machining of dowels, pins and screws from bone. F. Albee, *Bone Graft Surgery in Disease, Injury and Defor-*

*mity* p. 22 (1940); and F. Albee, *The Improved Albee Bone Mill*, American Journal of Surgery p. 657 (March 1938).

Accordingly, there is a need for implantable shaped structures made entirely out of cortical bone tissue that are larger than naturally occurring bone structures and are made wholly out of cortical tissue without using external, non-cortical fasteners or adhesives.

SUMMARY OF THE INVENTION

The present invention is directed toward a shaped structure made out of allograft cortical bone tissue that is larger than the natural dimensions of a cortical bone layer made by combining two or more smaller pieces to form a compound bone structure.

The compound bone structure is comprised of a first bone member having a first mating face constructed and arranged to support a load applied in a direction that is normal to the first mating face and to receive and engage a complimentary mating face of a second bone member. The second bone member has a mating face that is complimentary to the first mating face of the first bone member. The second mating face is constructed and arranged to support a load applied in the direction normal to the second mating face and to engage the first mating face so that the first and second bone members cooperate to form the compound bone structure.

The compound bone structure has an exterior surface that can be shaped to form an implant that can support the anatomical load and orient the implant in the surgical site so that the anatomical load is applied to the engaged first and second mating faces in the normal direction. Complimentary mating structures formed on the first and second mating faces prevent displacement of the first bone member with respect to the second bone member in both a longitudinal direction and a transverse when an anatomical load is applied.

At least one pin is placed through the component bone members of compound bone structure at an oblique angle to the plane of the mating faces and extends through the full thickness of the compound bone structure.

It is an object of the invention to make a compound bone structure from bone tissue of smaller bone segments for use in implantation into a surgical site and to support an anatomical load applied to the compound bone structure during a post-operative period while the implanted bone tissue is resorbed and remodeled.

It is another object of the invention to fabricate shapes out of allograft cortical tissue that would enable larger parts to be made out of cortical tissue without using external non-cortical fasteners or adhesives.

It is yet another object of the invention to form a compound bone structure which is implantable and is larger than bone pieces that are found in nature.

These and other objects, advantages, and novel features of the present invention will become apparent when considered with the teachings contained in the detailed disclosure along with the accompanying drawings.

DETAILED DESCRIPTION OF THE PREFERRED EMBODIMENT

Figure 1:
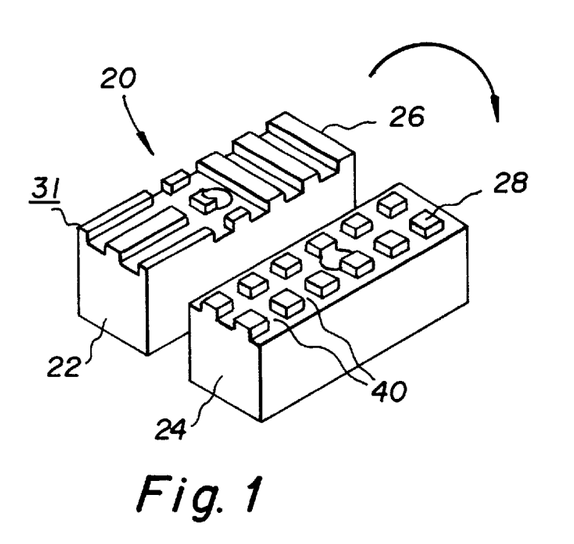
FIG. 1 shows an exploded flipped perspective elevational view of the inventive compound bone device.
Figure 2:
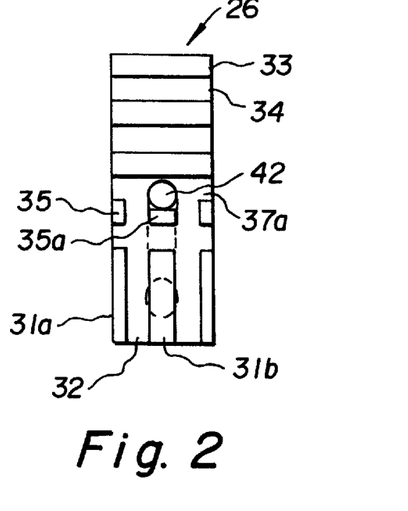
FIG. 2 shows a top plan view of one of the bone members of the inventive compound bone device shown in FIG. 1.
Figure 3:
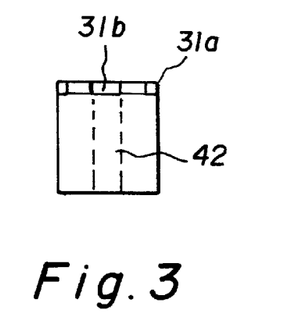
FIG. 3 shows an end elevational view of the bone member shown in FIG. 2.
Figure 4:
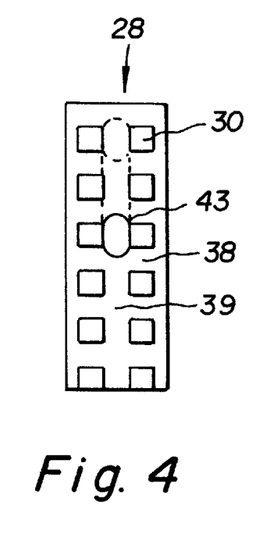
FIG. 4 shows a top plan view of a second member of the inventive compound bone device shown in FIG. 1.

The preferred embodiment and the best mode of the invention is shown in FIGS. 1–7. FIG. 1 shows an exploded side view of a compound bone device 20 with a first bone member 22 and a second bone member 24 flipped for viewing. The first and second bone members 22, 24 are constructed from rectangular blocks of bone tissue that have been machined or shaped by other suitable means. Each bone member 22, 24 has a mating face or engagement surface 26 and 28 as shown in FIGS. 2 and 4 respectively that has been shaped to form integral mating projections or teeth 30 on each face 26, 28 so that the members 22, 24 can be engaged to form the compound bone device 20 shown in FIG. 6.

Bone member 22 has a mating face 26 constructed with three bar projections 31 separated by grooves 32 formed on one end. The bar projections 31 run parallel to the longitudinal axis of the bar member and extend along the mating face less than ½ the length of the bar member. The grooves 32 are preferably around 2 to 2.12 mm in width and the side bars 31(*a*) have a width which is less than the width of the center bar 31(*b*). The other end of the bone member 22 has three bar projections 33 separated by grooves 34 running transverse the longitudinal axis and extending across the width of the bone member 22. The midsection of the bone member has a plurality of rectangular projections 35 formed by extending grooves 32 up to the side wall 36 of the inner transverse bar 33. The rectangular projections 35 are separated from the axially aligned bar members 31 by a groove 37 and the side wall 36 of inner transverse bar 33 by groove 37(*a*). The bars 31(*b*), 33 and center rectangular projection 35(*a*) have a width of approximately 2 mm.

Figure 5:
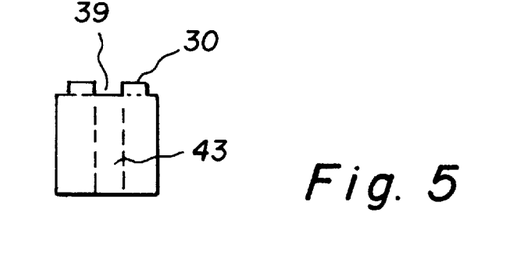
FIG. 5 shows an end elevational view of the bone member shown in FIG 4.
Figure 6:
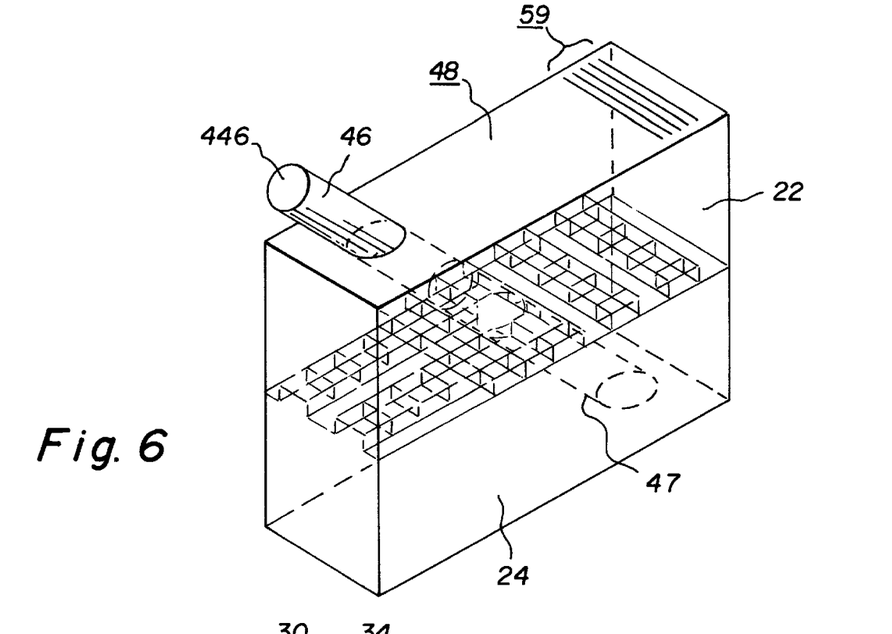
FIG. 6 shows an assembled perspective elevational view of the inventive compound bone device with the respective mating faces in phantom and an inserted dowel.
Figure 7:
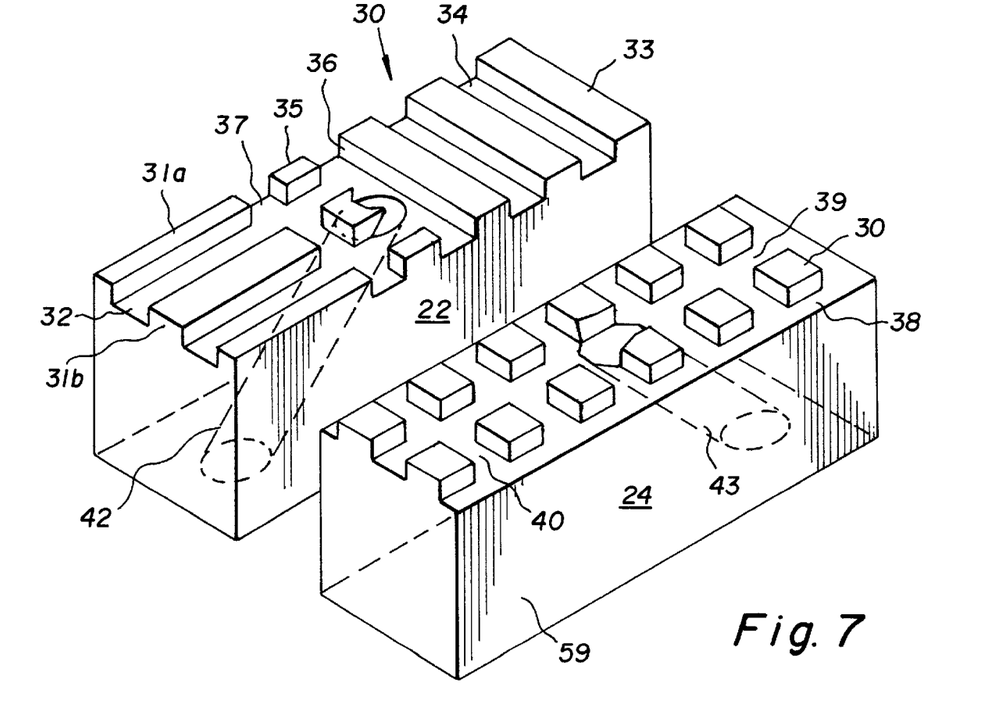
FIG. 7 shows an exploded flipped perspective view of the inventive compound bone device with dowel removed and the dowel bore in phantom.

Bone member 24 is formed with grooves 38 along each longitudinal side of the body and is also provided with a central groove 39 extending longitudinally the length of the bone member 24. Grooves 40 run across the width and transversely intersect grooves 38 and 39 forming projections 30. The grooves 38 located on opposite sides of the bone member 24 receive the side bars 31(a) and the side rectangular projections 35.

The mating projections or teeth range from 0.5 to 2.0 mm in height, preferably 1.0 mm and are formed by cutting a plurality of slots, grooves or channels ranging from 1 to 4 mm in width with a generally rectangularly shaped cross sections in each mating surface 26, 28 of the bone members. The channels or grooves 38–40 are of equal width dimensions and preferably have a width ranging from 2.0 mm to 2.12 mm apart.

The mating projections 30 and the channels on the bone members 22, 24 form complimentary inverse patterns that allow the members 22, 24 to be engaged or meshed together by press fitting the patterns together. This engagement and relationship of the various projections prevents relative motion between the members 22, 24 in both the transverse and longitudinal directions to stabilize the compound bone device 20 during subsequent machining of the exterior surface of the device 20 and during or after implantation in a surgical site.

Two biased or angled bores 42 and 43, respectively, extend through each bone members 22, 24. The bores 42 and 43 are shown in phantom in FIGS. 6 and 7. The bores 42 and 43 are oriented so that when the members 22, 24 are engaged, the bores 42 and 43 are axially aligned to form a continuous first bore 47 through the compound bone device 20. A cylindrical pin 46 shown in FIG. 6 preferably made of cortical bone tissue is press fit into the continuous bore 47 to prevent the separation of the members 22, 24.

Thus, the mating surfaces 26, 28 of the bone members 22, 24 are secured together by at least one pin positioned at an oblique angle to the plane of the engaged mating surfaces and extending the full thickness of the compound bone device 20. In the preferred embodiment shown in FIGS. 1–7, the wall surrounding bore 47 is cylindrical and pin 46 is cylindrical. The pin has a diameter slightly greater than the diameter of the bore 47 so that the pin is retained in the bore by an interference fit and is constructed with a tolerance of 0.03 mm to 0.25 mm with respect to the bore diameter. If desired a suitable medical adhesive can be use to insure that the pin stays in the bore during insertion.

It will be appreciated that three or more bone members can be fastened together by forming projections on both sides of the bone members. As an example, bone member 24 could be provided with an identical mating face on its opposite side which would engage another bone member shaped identical to bone member 22.

Figure 8:
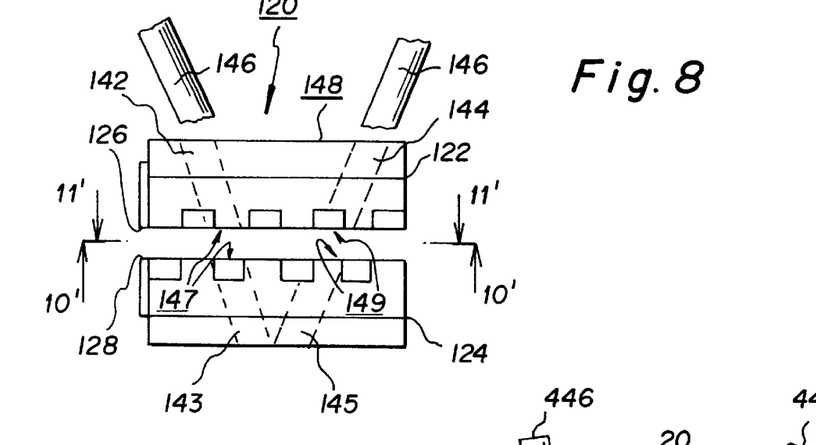
FIG. 8 shows an exploded side elevational view of another embodiment of the compound bone device.
Figure 10:
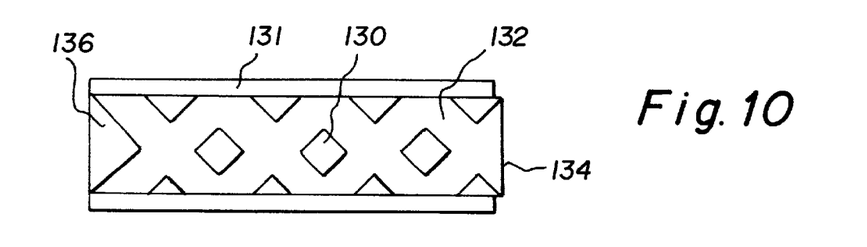
FIG. 10 is an plan view of the first bone member taken along line 10'—10' in FIG. 8.
Figure 11:
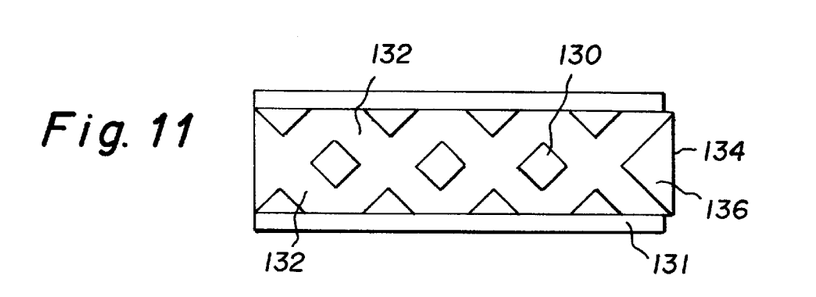
FIG. 11 is a plan view of the second bone member taken along line 11'—11' in FIG. 8.

FIG. 8 shows an alternative embodiment of the compound bone device 120 constructed with a first bone member 122 and a second bone member 124. The first and second bone members 122, 124 are constructed from rectangular blocks of bone tissue that has been machined or shaped by other suitable means. Each bone member 122, 124 has a mating face or surface 126 and 128 as shown in FIGS. 10 and 11 respectively that has been shaped to form integral mating projections or teeth 130 on each face 126, 128 so that the members 122, 124 can be engaged to form the compound bone device 120 shown in FIG. 9.

Figures 9, 14:
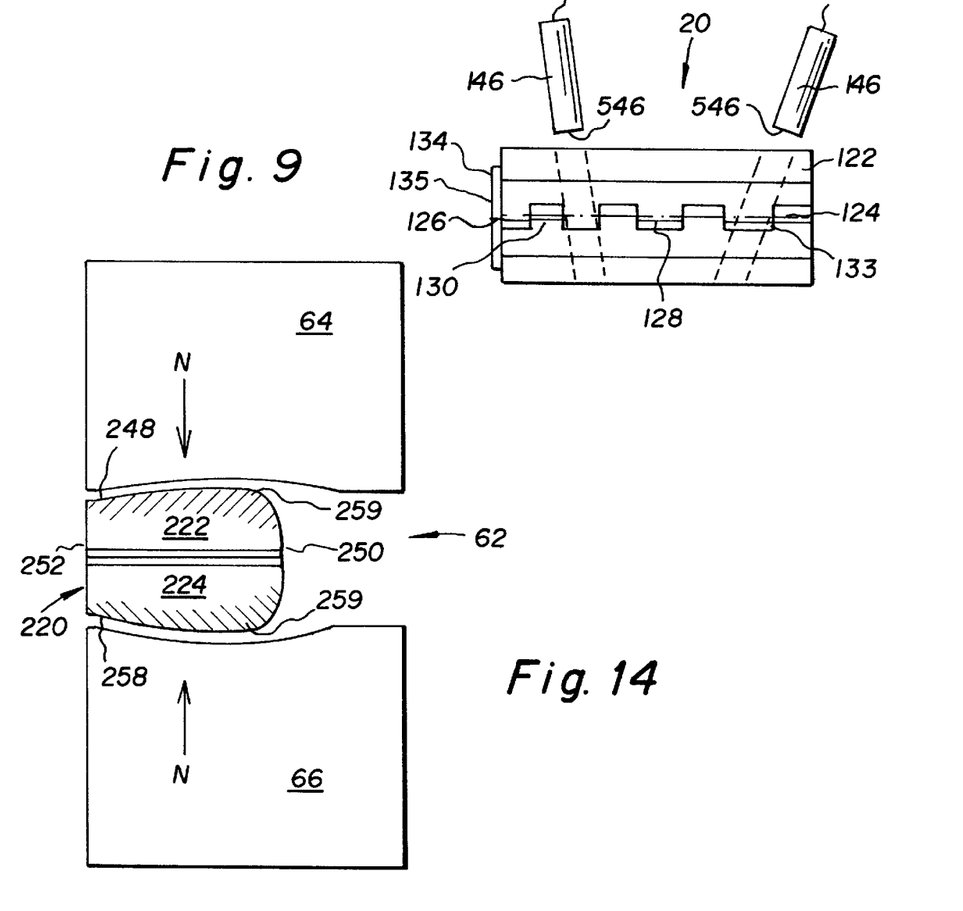
FIG. 9 is an assembled side elevational view of the compound bone device of FIG. 8 showing the dowels removed and dowel bores in phantom.
FIG. 14 is a schematic view of the compound bone device shown in FIGS. 12 and 13 in a surgical site formed between an upper and a lower vertebrae in lumbar portion of a spine.
Figure 12:
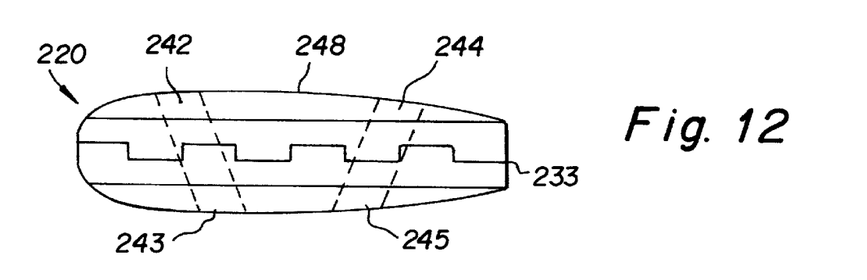
FIG. 12 is a side elevational view of the compound bone device shaped to form an implant for insertion between vertebra for spinal fusion with the bores shown in phantom.

Each bone member 122, 124 has been shaped to form a groove 131 on each longitudinally extending side of each member so that when the members are engaged as shown in FIGS. 9 and 12, a composite groove 133 extends longitudinally the length of the compound bone device 120. The groove 133 is located on opposite sides of the compound bone device 120 and serves as a holding slot for the instrument which holds the compound bone device 120 while it is being machined. One end of each bone member 122, 124 has been machined to provide a slightly extended end surface 134. The raised end surfaces 134 cooperate when the members 122, 124 are engaged to form an impact surface 135 that can be struck with a hammer or other suitable instrument during a surgical procedure to implant the compound bone device 120 into a surgical site.

The mating projections or teeth 130 range from 0.5 to 2.0 mm in height, preferably 1.0 mm and are formed by cutting a plurality of slots, grooves or channels 132 ranging from 1 to 4 mm in width with a generally rectangular shaped cross section in each mating surface 126, 128 of the bone tissue. The channels 132 are of equal dimensions and are preferably equally spaced about 2.0 mm to 2.12 mm apart. The channels 132 are preferably angled at +45 degrees and −45 degrees with respect to the longitudinally extending grooves 131.

The mating projections or teeth 130 formed by the channels 132 are comprised of a plurality of identical longitudinally spaced rectangular projections in a central portion of each mating surface 126, 128. A larger triangular shaped projection 136 extends transversely between the longitudinal edges at one end of each of the mating surface 126, 128. The triangular shaped projection 136 has the same height as the projections 130.

The mating projections 130 and the channels 132 on the bone members 122, 124 form complimentary inverse patterns that allow the members 122, 124 to be engaged or meshed together by press fitting the patterns together. This engagement prevents relative motion between the members 122, 124 in both the transverse and longitudinal directions to stabilize the compound bone device 120 during subsequent machining of the exterior surface of the device 120 and during or after implantation in a surgical site.

As shown in FIGS. 10 and 11, the channels 132 are machined in the cortical bone to preferably a 1 mm depth and are angled at +45 degrees and −45 degrees in relation to edge 131 of each member 122, 124. The plus and minus 45 degree angles are the preferred angles for forming complimentary patterns on each surface 122, 124 because of ease of manufacturing, but any angle within a range of from about 15 degrees to about 75 degrees could be used in a similar way to cut other patterns forming mating surfaces 126, 128. It is understood that a degree of tolerance is necessary in the manufacturing process to assure that the members 122, 124 can be engaged and still provide sufficient structural support to the compound bone device 20. In all of the described embodiments, the maximum tolerance between the engaged parts at the surface ranges from 0.025 mm to 0.1 mm.

Two biased or angled bores 142, 144 and 143, 145, respectively, extend through each bone member 122, 124. The bores 142, 144, 143, 145 are shown in phantom in FIGS. 8 and 9. The bores 142, 144, 143, 145 are arranged so that when the members 122, 124 are engaged, the bores 142, 144, 143, 145 are axially aligned to form a continuous first bore 147 and a continuous second bore 149 through the compound bone device 120. Two cylindrical pins 146 shown in exploded view in FIG. 8 preferably made of cortical bone tissue are press fit into each the continuous bores 147, 149 to prevent the separation of the members 122, 124.

Thus, the mating surfaces 126, 128 of the bone members 122, 124 are secured together by at least one pin positioned at an oblique angle to the plane of the engaged mating surfaces and extending the full or partial thickness of the compound bone device 120. The wall surrounding each bore 147, 149 is cylindrical and each pin 146 is cylindrical. The pin has a diameter slightly greater than the diameter of the bores 147, 149 so that the pins are retained in the bores by an interference fit and is constructed with a tolerance of 0.03 mm to 0.25 mm with respect to the bore diameter. If desired a suitable medical adhesive can be use to insure that the pins stay in the bores during insertion. It can be appreciated that the bores and pins can have other configurations as, for example, rectangular, triangular and the like.

When the bone members 122, 124 are engaged and the pins 146 are inserted to hold them together, an exterior surface 148 of the compound bone device 120 can be shaped to form a suitable implant device for implantation into a surgical site. If desired, the exterior surface 48, 148, 248, 348 can be scored 59, 259 or otherwise configured to present gripping means which grips surrounding tissue when the compound bone device is implanted into the surgical site. The pins 146 provide sufficient structural reinforcement for the compound bone device to allow the device 120 to be machined to form the desired shape.

Figure 15:
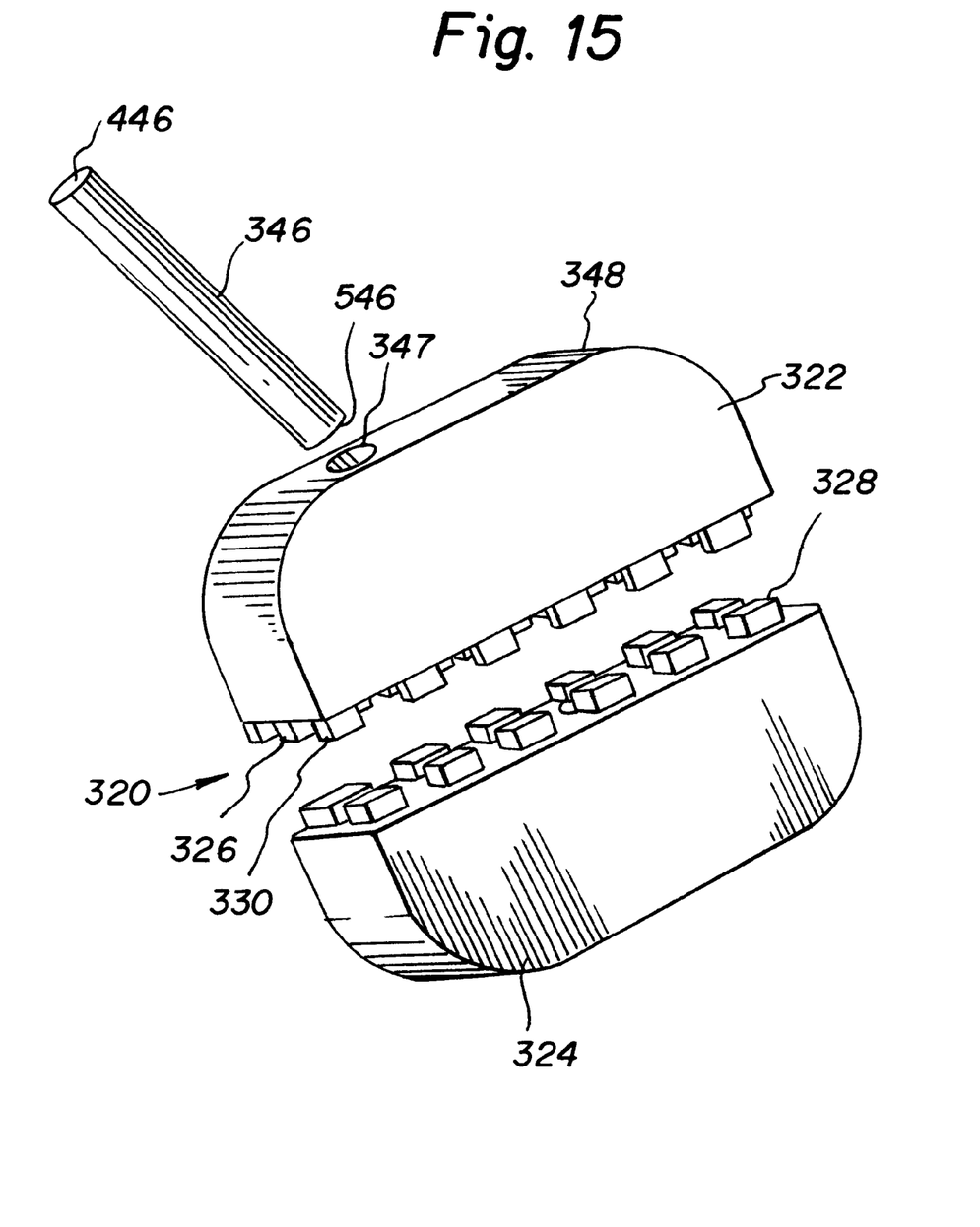
FIG. 15 is an exploded perspective view of an alternative embodiment of a smooth outer surfaced compound bone device.

Another compound bone device 220 is shaped so that when the device 220 is implanted in a surgical site, the anatomical load of the patient is applied in a direction that is normal to the engaged mating faces 226, 228. The normal direction is shown in FIG. 15 by an arrow N. It can be appreciated from the cross-section that when the two members 222, 224 are engaged, the projections on the first member 222 are disposed between or adjacent channels on the second member 224 to prevent the relative movement between the members 222, 224 in the longitudinal and transverse directions. There are some empty spaces between the mating faces 226, 228 of the compound bone device 220.

Figure 13:
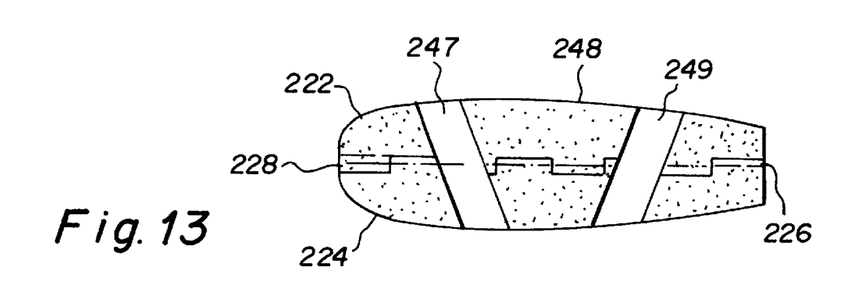
FIG. 13 is a cross-sectional view of the compound bone device of FIG. 12 taken along the center axis of the device.

FIGS. 12, 13 and 14 show that the exterior surface 248 of the compound bone device 220 can be shaped to form a intervertebral implant for the lumbar spine for insertion between vertebrae to fuse the vertebrae. The compound bone device 220 can be machined to provide a sloped and rounded proximal end 240 and distal end 252 for easy intervertebral insertion.

FIG. 13 shows a cross-section of a compound bone device 220 taken through FIG. 12. The cross-section shows that the bores 247, 249 are angled with respect to the normal direction N. It can be appreciated that the normal direction is generally perpendicular to each of the engaged surfaces of the compound bone device 220. Each mating face 226, 228 is constructed and arranged to support a load that is applied in a direction that is normal to the surface. When the surfaces are engaged they can support an applied normal load and, because they are engaged, the normal load will not displace the bone members 222, 224 in the longitudinal or transverse directions relative to one another.

The bores 247, 249 generally form oblique angles with the engaged surfaces. It can be appreciated from FIGS. 12 and 13 that the oblique angles of the bores 247, 249 are complimentary. That is, the angle of bore 247 is the inverse of or the negative of the angle of bore 249. The preferred angle of bore 247 with a line generally extending between the two faces is about 110 degrees and therefore the angle of bore 249 is negative 110 degrees.

FIG. 14 shows a schematic representation of the compound bone device 220 implanted in a surgical site 62 in the lumbar spine between an upper vertebra 64 and a lower vertebra 66 to fuse the vertebra. In this surgical procedure, an intervertebral space is enlarged and shaped to receive the allograft compound bone device 220 implant. The compound bone device 220 is inserted in the surgical site 62 so that the applied anatomical load N is applied in a direction that is normal or perpendicular to the engaged mating faces 226, 228.

The exterior surface 248 of the compound bone device 220 is shaped to support the applied load in a direction that is normal to the engaged faces 226, 228 and to maintain the orientation of the implanted compound bone device 220 in the surgical site 62 throughout the post-operative period.

The engaged faces 26, 28, 126, 128, 226, 228 and 326, 328 support the major anatomical load of the patient during the post operative recovery period. The engagement between the respective projections 30, 130, 230 and 330 on the two mating faces 26, 28, 126, 128, 226, 228 and 326, 328 assure that the first and second bone members 22, 24, 122, 124, 222, 224 and 322, 324 do not move relative to one another in the longitudinal or transverse directions during the post operative period.

It is desired that the compound bone devices 20, 120, 220 and 320 hold together during the post operative period to allow resorption and remodeling to occur in the allograft tissue and pins are used to hold the same together. The pins 46, 146 (pins 246 not shown), 346 inserted in bores 47; 147, 149, 247, 249 and 347 can be made of cortical, allograft tissue. The outer surface of each cortical pin is entirely within and surrounded by the bone mass of the compound bone device so that the pin is substantially protected from the biochemical attack that occurs from normal biological and biochemical processes as the implant is integrated into the bone of the patient. Only the end surfaces 445 and 546 of the pin 46, 146 are exposed, but this results in minimal structural degradation of each pin.

The biological and biochemical process cause a slow absorption of the implanted bone to occur over time. This absorption could structurally degrade the interlocking bone members of the compound bone device. Because the anatomical load is normal to the mating complimentary surfaces, the anatomical load can be sustained even during tissue degradation. Because the pins are substantially protected from the biochemical mechanism of absorption, the pins will continue to secure the bone members together long enough to allow full healing and integration to occur. The cortical pins 46, 146 and 346 are embedded and held tightly in the mass of the implant and are protected from the biochemical attack of the patient except at the two end surfaces 446 and 546 of each pin. The pins 46, 146, and 346 remain structurally intact during the post-operative period to help maintain the structural stability of the compound bone device 20, 120, 220 and 320.

The normal absorption mechanisms that occur during the healing process also tend to structurally degrade the two engaged bone members of the compound bone device 20, 120, 220 and 320 during the post operative period. Because the anatomical load is normal to the engaged surfaces, the applied load can be supported by the device 20, 120, 220 and 320 even though some degradation of the allograft tissue does occur. Because the length of the interlocking pins 46, 146 and 346 are protected from biochemical degradation, the pins continues to secure and hold the two bone members 22, 24; 122, 124; 222, 224 and 322, 324 in place long enough for full resorption and remodeling to occur. The cortical tissue of the compound bone device 20, 120, 220, and 320 has been observed to last 6 to 12 months before being fully integrated into the host patient.

The assembled compound bone device 220 shown in the schematic view in FIG. 14 was tested in a cadaver lab in which it was inserted into the lumbar spine. The procedure requires that the assembly be hammered using considerable force into the intervertebral disc space. Four compound bone devices were successfully inserted into the spine with no signs of impact damage due to the insertion.

Another embodiment of the compound bone device 320 is shown in FIG. 15 which shows a first bone member 322 and a second bone member 324 in exploded view with a pin 346. The mating faces 326, 328 and projecting teeth 330 can be engaged and secured together with pin 346 to form the compound bone device 320. The exterior 348 has been shaped to form a rectangular shape with rounded corners.

It can be understood by one skilled in the art that the preferred embodiment described above is intended as an example only to teach the broad principles of the invention and is not intended to be limiting. It can be understood, for example, that the mating projections or teeth 30, 130, 230, 330 are constructed and arranged so that when the two mating faces 26, 28 and 126, 128 and 226, 228 and 326, 328 are engaged, there is no significant relative movement between the bone members in the longitudinal and transverse directions outside of that permitted by the manufacturing tolerances and by any structural changes that occur in the bone device during the post operative period.

It is appreciated that many geometric configurations of projections on each mating face can provide suitable structures to prevent relative movement between the bone members in the longitudinal and transverse directions.

In general, a plurality of mating projections and channels forming mating spaces are provided on a first mating face and a plurality of mating projections and mating spaces are provided on a second mating face. When the faces are engaged or mated, the mating teeth on the first face are disposed within the mating spaces on the second mating face and the mating teeth on the second mating face are disposed within the mating spaces on the first mating face to prevent the relative movement between the bone members in the longitudinal and transverse directions when the bone members are inserted into a surgical site or are disposed in a surgical site during a post operative period.

In general, each mating face is constructed and arranged to support an applied load applied in a normal direction and to engage a mating face with complimentary projection receiving construction.

The two piece design for the compound bone devices described above allow for constructions 10 mm×25 mm or larger. This assembly technique considerably broadens the use of allograft tissues by allowing much larger implants to be formed than could have been attained from the normal human anatomy.

It can also be understood that because the preferred embodiment is illustrative only, as it is contemplated to provide a compound bone device comprised of more than two bone members. In such a case, the compound bone device can be thought of as being comprised of an upper member, a middle member(s) and a lower member. The upper and lower members are provided with a single mating face and the middle member(s) is provided with two mating faces generally disposed on opposite sides thereof so that the three or more bone members or pieces can be engaged and pinned together with at least one embedded cortical bone pin, preferably located at an oblique angle to the longitudinal plane of the mating surfaces.

Because bones are irregularly shaped and because not all applications of the invention require that the implant support an anatomical load that is applied in generally one direction, it can be understood that if more than one pair of engaged mating faces is present in a single compound bone device, the pairs need not necessarily be parallel nor do the individual members of each pair have to be generally planar to form a compound bone device.

The compound bone device can be constructed and arranged to support a load applied in a direction that is generally normal to the two pairs of engaged faces so that the bone device can support an anatomical load and prevent the relative displacement of the three bone pieces in a longitudinal or transverse direction.

It can further be understood that because the illustrated embodiment is exemplary only, it is contemplated to provide compound bone devices which are shaped for many applications and that the compound bone device design is not restricted to use in the lumbar spine for spinal fusion. A compound bone device comprised of two or more bone members can be shaped during the manufacturing process to form compound bone pins, bone screws, plates, discs, wedges, blocks and other devices of various configurations.

The compound bone device can be fabricated from xenograft, autograft or allograft bone tissue, and it is contemplated to use any suitable bone tissue from any source to form a compound bone device.

It is also understood that although it is preferred to fabricate the compound bone device using only cortical bone without the use of adhesives or synthetic absorbable or nonabsorbable polymers or metals, it is within the scope of the invention to additionally secure together the bone members with any suitable surgical bone adhesive or with a synthetic absorbable or nonabsorbable polymer or in any combination with or without at least one pin made of bone tissue.

In the foregoing description, the invention has been described with reference to a particular preferred embodiment, although it is to be understood that specific details as shown are merely illustrative, and the invention may be carried out in other ways without departing from the true spirit and scope of the following claims.

What is claimed is:

1. A compound bone device made from sterile bone tissue for implantation into a surgical site which supports an anatomical load applied to the compound bone device during a post-operative period while the implanted bone tissue is being resorbed and remodeled, comprising:

a first bone member defining a first mating face constructed and arranged to support a load in a direction that is normal to the first mating face and to receive and engage a complimentary mating face of a second bone member;

a second bone member defining a second mating face that is complimentary to the first mating face of the first bone member constructed and arranged to support a load in the direction normal to the second mating face, said mating faces being mounted to each other so that the first and second bone members form a compound bone device which prevents displacement of the first bone member with respect to the second bone member in both a longitudinal direction and a transverse direction when an anatomical load is applied;

each bone member defining a bore within its body which is angularly oriented with respect to a plane across its mating face and opens on said mating face, each bore being axially aligned with an angularly oriented bore defined in the body of the other bone member and a cortical pin member mounted in said axially aligned bores extending across said mating face in an interference fit to hold the first and second bone members in engagement resisting separation of the first and second bone members.

2. A compound bone device made from bone tissue as claimed in claim 1 wherein each bone member has a body which defines at least two angularly positioned bores which are axially aligned with the angularly positioned bores of the other bone member, said bores being orientated at an oblique angle to a plane of each engaged mating surface and intersecting the plane of the mating surface and a pin member mounted in each of the aligned bores.

3. A compound bone device made from bone tissue as claimed in claim 1 wherein each said pin member is cylindrical in shape and has a length equal to or less than the length of the aligned bores of the respective bone member bodies.

4. A compound bone device made from bone tissue as claimed in claim 1 wherein said bone device is an implant for insertion between vertebra so that the anatomical load is normal to the engaged first and second mating faces to effect intervertebral fusion during the post operative period.

5. A compound bone device made from bone tissue as claimed in claim 1 wherein one of the mating faces defines a plurality of bar members substantially parallel to the longitudinal axis of bone members and a plurality of bar members oriented transverse to the axis of the parallel bar members.

6. A compound bone device made from bone tissue as claimed in claim 1 wherein a cross-section of the compound bone device in the normal direction is at least 10 mm by about 25 mm.

7. A compound bone device made from bone tissue as claimed in claim 2 wherein a first pin is disposed through the engaged mating faces at a first angle and a second pin is disposed through the engaged mating faces at a second angle.

8. A compound bone device made from bone tissue as claimed in claim 7 wherein said first angle is the inverse of the second angle.

9. A compound bone device made from bone tissue as claimed in claim 1 wherein said compound bone device body has a substantially cylindrical shape with rounded ends with an exterior wall of the body including gripping means constructed and arranged to grip tissue when the compound bone device is implanted into the surgical site.

10. A compound bone device made from bone tissue as claimed in claim 1 wherein said device has a substantially rectangular shape with rounded ends.

11. A compound bone device made from bone tissue for implantation into a surgical site which supports an anatomical load applied to the compound bone device during a post-operative period while the implanted bone tissue is being resorbed and remodeled, comprising:
 a first bone member defining a first mating face constructed and arranged to support a load in a direction that is normal to the first mating face and to receive and engage a complimentary mating face of a second bone member;
 a second bone member defining a second mating face that is complimentary to the first mating face of the first bone member and is constructed and arranged to support a load in the direction normal to the second mating face, said mating faces being mounted to each other so that the first and second bone members form a compound bone device which prevents displacement of the first bone member with respect to the second bone member in both a longitudinal direction and a transverse direction when an anatomical load is applied, said first mating face defining at least one substantially planar surface and being provided with a plurality of intersecting channels to form a plurality of mating projections which define a first pattern thereon sand said second mating face has at least one substantially planar surface and is constructed with a plurality of intersecting channels to form a second plurality of mating projections which define a second pattern thereon that is complimentary to the first pattern on the first planar face so that the first and second bone members can be engaged to prevent relative movement therebetween in the longitudinal and transverse directions when the compound bone device is supporting an anatomical load.

12. A compound bone device made from bone tissue as claimed in claim 11 wherein said plurality of intersecting channels comprises of a first set of equally spaced channels angled at about +45 degrees to an edge of each mating face and a second set of equally spaced channels angled at about −45 degrees to the edge of each mating face to form complimentary mating pattern.

13. A compound bone device made from bone tissue as claimed in claim 11 wherein the maximum tolerance between channels and projections of the first and second mating faces when the first and second bone members are engaged is about 0.2 mm.

14. A compound bone device made from bone tissue as claimed in claim 12 wherein the channel depth ranges from about 0.5 mm to about 2.0 mm and the channel width ranges from about 1.0 mm to about 4.0 mm.

15. A compound bone device made from bone tissue as claimed in claim 11 wherein the plurality of channels is comprised of a first set of equally spaced channels disposed at an angular value selected from the range of about 15 degrees to about 75 degrees with respect to an edge of each mating face and a second set of equally spaced channels disposed at an angle with respect to the edge of each mating face that is the negative of the angular value selected for the first set of equally spaced channels to form a mating pattern in the first and second mating faces.

16. A compound bone device made from bone tissue as claimed in claim 11 wherein the mating projections have a rectangular cross section with at least one mating projection positioned adjacent the end of a mating face and having a triangular configuration.

17. A compound bone device made from bone tissue for implantation into a surgical site which supports an anatomical load applied to the compound bone device during a post-operative period while the implanted bone tissue is being resorbed and remodeled, comprising:
 a first bone member defining a first mating face constructed and arranged to support a load in a direction that is normal to the first mating face and to receive and engage a complimentary mating face of a second bone member;
 a second bone member defining a second mating face that is complimentary to the first mating face of the first bone member and is constructed and arranged to support a load in the direction normal to the second mating face, said mating faces being mounted to each other so that the first and second bone members form a compound bone device which prevents displacement of the first bone member with respect to the second bone member in both a longitudinal direction and a transverse direction when an anatomical load is applied wherein one of said mating faces defines a plurality of substantially square shaped projections and the other mating face defines a plurality of bar shaped projections which are seated adjacent said square shaped projections when the mating faces are joined together.

18. A composite allograft bone device constructed of a plurality of bone members comprising a first bone member body defining with a face that includes a plurality of intersecting grooves cut into the face of the body to define a plurality of spaced projections; a second bone member body defining a face that includes a plurality of intersecting grooves cut into the face to form a plurality of spaced projections, said projections on said second face fitting into grooves cut in said first face and said projections on said first face fitting into grooves cut in said second face allowing the two bodies to be mated together, said mated bodies forming a composite bone device defining at least one throughgoing bore which is positioned at an angle to the longitudinal axis of said composite device and a pin mounted in each said throughgoing bore extending into said bodies precluding the bodies from relative longitudinal movement.

19. The composite device of claim 18 wherein said grooves are orthogonal.

20. The composite device of claim 18 wherein the majority of said projections have a rectangular profile with a planar top surface.

21. The composite device of claim 18 including at least one projections with a triangular profile having a planar top surface.

22. The composite device of claim 18 wherein said first bone body face and said second bone body face have two grooves which run along the side edges of the bone member body.

23. The composite device of claim 18 including a third bone member body defining two faces, each face including a plurality of intersecting grooves cut into the surface of the body to define a plurality of spaced projections, said projections of said faces fitting into grooves cut in said first face and said second face allowing the three bodies to be mated together.

24. The composite device of claim 18 wherein said grooves intersect at about a 45° angle.

25. The composite device of claim 18 wherein each of said projections has a diamond configuration.

26. The composite device of claim 18 wherein said projections have a height of about 1.0 mm.

27. A sterile composite bone assembly made from allograft bone tissue comprising a plurality of bone members, each bone member comprising a body defining an exterior surface and at least one mating face defining a plurality of spaced projections which interlock and fit within spaces formed between the projections of a mating face of another bone member and at least one pin member mounted in a bore formed in a body of each bone member extending at an angle across the interlocked mating faces with said at least one pin member extending past the mating faces but not extending past the exterior surface of the bone member body.

28. The composite bone assembly of claim 27 wherein said plurality of bone members comprises at least three bone members.

29. A compound bone structure made from allograft bone tissue constructed for implantation into a surgical site which supports an anatomical load applied to the compound bone structure during a post-operative period during which the implanted bone tissue is resorbed and remodeled, comprising:

a first bone member formed with a first mating face that defines a plurality of spaced mating teeth extending therefrom forming a first pattern with a plurality of bar shaped teeth which run in a longitudinal direction and a plurality of bar shaped teeth which run in a direction traverse to the longitudinal direction on the first bone member and defining a shaped outer surface;

a second bone member formed with a second mating face that defines a plurality of spaced mating teeth extending therefrom forming a second pattern that is complimentary to the first pattern on the first mating face in that the teeth fit in spaces between the teeth of the first mating face and defining a shaped second outer surface;

the first and second bone members being engaged by a press fit so that when the first mating face engages the second mating face, the first and second bone members form the compound bone structure and the first and second outer surfaces cooperate to form an exterior surface of the compound bone structure, said exterior surface being shaped to form an implant which can be implanted via force into the surgical site so that when an anatomical load is applied to the implanted compound bone structure in a direction that is normal to the first and second mating faces, relative movement is precluded between the first and second bone members in a longitudinal direction and in a transverse direction.

30. A compound bone structure made from allograft bone tissue as claimed in claim 29 wherein the compound bone structure further includes a first bore that extends from the first outer surface through the first and second mating faces and through the second outer surface and a second bore that extends from the first outer surface through the first and second mating faces and through the second outer surface and a first pin having a first end and a second end, said first pin being disposed in the first bore from the first outer surface to the second outer surface and retained therein by an interference fit and a second pin having a first end and a second end, the second pin being disposed in the second bore from the first outer surface to the second outer surface and retained therein by an interference fit with said first and second pins being embedded in the compound bone structure so that when the compound bone structure is implanted in the surgical site only the first and second ends of the first and second pins are exposed to biochemical attack during the post operative period.

31. A compound bone structure made from allograft bone tissue as claimed in claim 29 wherein the first mating face has a first side edge and a parallel second side edge and has a plurality of equally dimensioned and equally spaced slots angled at about +45 degrees to said edges and a plurality of equally dimensioned and equally spaced slots angled at about −45 degrees to said edges to define the first pattern on the first mating face and wherein the second mating face has similarly spaced slots to define a second pattern on the second mating face that is complimentary to and mates with the first pattern.

32. A compound bone structure made from allograft bone tissue as claimed in claim 30 wherein the first bore is disposed at an oblique angle that defines a first angular value with the engaged mating surfaces and a wherein the second bore is disposed at an oblique angle that defines a second angular value that is the inverse of the first angular value with the engaged mating surfaces.

33. A compound bone structure made from allograft bone tissue as claimed in claim 29 wherein the first essentially planar mating face has a first edge and has a plurality of equally dimensioned and equally spaced slots angled at a selected slot angular value that is selected from a range of from about +15 degrees to about +75 degrees to the first edge and a plurality of equally dimensioned and equally spaced slots angled at a slot angular value that is the inverse of the selected slot angular value to the first edge to define the first pattern on the first mating face and wherein the second essentially planar mating face has a second edge and has a plurality of equally dimensioned and equally spaced slots angled at a selected slot angular value that is selected from a range of from about +15 degrees to about +75 degrees to the second edge and a plurality of equally dimensioned and equally spaced slots angled at an angle that is the inverse of the selected slot angular value to the first edge to define the first pattern on the first mating face.

34. A compound bone structure made from allograft bone tissue as claimed in claim 29 wherein the first mating face has a first end and a second end and wherein the first pattern on the first mating face is comprised of a plurality of equally spaced rectangular structures arranged in a longitudinally extending rows, and a plurality of equally spaced rectangular structures arranged in transversely extending rows and the second mating face has a first end and a second end and wherein the second pattern on the second mating face is comprised of a plurality of substantially identical equally spaced rectangular structures arranged in longitudinally extending rows, allowing the first mating face and the second mating face to be engaged so that spaced rectangular structures are positioned adjacent a corresponding row of structures on the opposing face.

35. A compound bone structure made from allograft bone tissue as claimed in claim 29 wherein the exterior surface is shaped to form an implant for posterior lumbar intervertebral fusion for insertion between upper and lower vertebrae to fuse the vertebrae.

36. A compound bone structure made from allograft bone tissue as claimed in claim 29 wherein the exterior surface is provided with a gripping structure constructed and arranged to grip tissue after implantation in the surgical site to prevent the compound bone structure from moving within the surgical site during the post operative period.

37. A sterile compound bone structure made from allograft bone tissue constructed and arranged for implantation into a spinal surgical site and to support an anatomical load applied to the compound bone structure by the spinal column during a post-operative period in which the implanted bone tissue is resorbed and remodeled, comprising:

a first bone member defining a body with a first exterior surface and a first mating face constructed to receive and engage a complimentary mating face;

a second bone member defining a body with a second exterior surface and a second mating face that is complimentary to the first mating face of the first bone member to receive and engage the first mating face so that the first bone member and the second bone member form a compound bone structure with the first and second exterior surfaces being shaped to form an intervertebral implant for insertion between adjacent upper and lower vertebrae for spinal fusion wherein the exterior is constructed and arranged to orient the implanted compound bone structure in the surgical site so that when the anatomical load is supported by the compound bone structure it is applied in a normal direction to the engaged first and second mating faces to prevent the displacement of the first bone member with respect to the second bone member in both a longitudinal direction and a transverse direction and a plurality of pins mounted in angular bores cut in said bone member bodies, each pin having a first end surface and a second end surface and being embedded within the compound bone structure so that the first pin end surface extends past the engaged first and second mating faces with the second pin end surface being positioned adjacent to or recessed from the exterior surface so that an end portion of the second end surface is exposed to biochemical degradation during the post operative period.

38. A sterile composite bone assembly made from a plurality of pieces of allograft bone tissue comprising a plurality of shaped bone members mounted together, each of which is provided with at least one mating face with a planar base surface, a plurality of spaced projections extending from said planar base surface, said projections being provided with a planar top which is parallel to said planar base surface and which engages the planar base surface of the opposing bone member and fits within spaces formed between the projections of a mating face of an opposing bone member.

39. A sterile composite bone assembly made from a plurality of pieces of preshaped bone tissue comprising a plurality of shaped bone members, each of which is provided with at least one mating face comprising a plurality of intersecting channels defining spaced projections which interlock and fit within spaces formed between the projections of a mating face of an adjacent shaped bone member to prevent horizontal movement in an axial direction and direction transverse to the axial direction with respect to each other.

40. A composite bone assembly comprising a plurality of bone members, each bone member defining at least one mating face with a plurality of spaced projections which interlock and fit within spaces formed between the projections of a mating face of another bone member, at least one of said bone members mating face projections comprising a plurality of projections with different sized rectangular geometric configurations, each bone member defining at least one bore which opens over a mating face and is orientated at an acute angle thereto and at least one pin mounted in said at least one bore.

41. A sterile composite allograft bone device constructed of a plurality of sterile bone members comprising a first sterile bone member body with a mating face, said mating face defining a plurality of intersecting channels and a plurality of spaced projections; a second sterile bone member body with a mating face, said mating face defining a plurality of intersecting channels and a plurality of spaced projections, said projections on said second mating face fitting into channels of said first mating face and said projections on said first mating face fitting into channels of said second mating face allowing the bone member bodies to be mated together forming a sterile composite bone device, said sterile composite bone device defining at least one bore which is oriented at an angle to the longitudinal axis of said composite device and and intersects the mating faces of the mated bone member bodies and a pin mounted in each said bore extending into said bone member bodies precluding said bone member bodies from relative movement with respect to each other.

42. A composite bone assembly comprising a plurality of bone members, each bone member defining at least one mating face with a plurality of spaced projections extending from the mating face which interlock and fit within spaces formed between the projections of a mating face of another bone member, at least one of said bone members mating face projections comprising a plurality of projections with end surfaces in the same plane and configured in different sized rectangular geometric configurations, each bone member defining at least one bore which opens over a mating face and is positioned angularly thereto and at least one pin mounted in said at least one bore, the outer end surfaces of each pin being located within said composite bone assembly.

43. A sterile composition bone implant made from a plurality of pieces of preshaped bone tissue adapted to be mechanically mounted together in a fixed relationship comprising a plurality of shaped bone members, each of which is provided with at least one mating face defining a planar base surface, a plurality of at least (9) spaced projections having vertical side walls extending from said planar base surface, said projections being formed with a planar top which engages the planar base surface of the opposing bone member and fits within spaces formed between the plurality of spaced projections of a mating face of another bone member, said mechanically mounted shaped bone members forming a bone implant having a body cross section in the normal direction of at least 10 mm.

44. A sterile composite bone assembly made from a plurality of pieces of preshaped cortical bone tissue comprising a plurality of shaped bone members, each of which is provided with at least one mating face comprising a plurality of spaced projections forming a pattern which interlocks and fits within spaces formed between the projections of a mating face formed in a complimentary inverse pattern on another adjacent bone member, mechanical fastener means engaging at least two of said shaped bone members, said bone shaped members when mounted together forming a substantially rectangular shape with rounded corners.

45. A sterile composite bone assembly made from a plurality of pieces of preshaped bone tissue comprising a plurality of shaped bone members, each of which is provided with at least one mating face comprising a planar base and a plurality of spaced projections which extend from said planar base, said spaced projections having a planar top surface which is parallel to said planar base and vertical walls which are substantially perpendicular to said top surface and said planar base allowing same to interlock and fit within spaces formed between the projections of a mating face of other similarly configured bone members, said bone members being connected with at least one mechanical fastener.

46. A sterile composite allograft bone device comprising a first bone member body defining with a face that includes a plurality of intersecting grooves cut into the face of the body to define a plurality of spaced projections forming a pattern and at least a second bone member body defining a face that includes a plurality of intersecting grooves cut into the face to form a plurality of spaced projections forming a second pattern, said plurality of spaced projections on the one bone face fitting into grooves cut in the other bone face allowing the bodies to be mated together, said mated bodies forming a composite bone device which is provided with at least one bore extending across the mating surface of the bodies and positioned at an acute angle to a plane formed across a mating face of the mated bone member bodies and a dowel mounted in said bore in an interference fit extending into the respective bone member bodies precluding the same from relative axial movement.

* * * * *

UNITED STATES PATENT AND TRADEMARK OFFICE
Certificate

Patent No. 6,025,538

Patented: February 15, 2000

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Joseph A. Yaccarino, III, Somerset, NJ; David C. Paul, Phoenixville, PA Signed and Sealed this Eighth Day of January 2002.

CORRINE M. MCDERMOTT
*Supervisory Patent Examiner*
Art Unit 3738